US00PP15109P2

(12) United States Plant Patent
Lyrene

(10) Patent No.: US PP15,109 P2
(45) Date of Patent: Aug. 24, 2004

(54) BLUEBERRY PLANT CALLED 'SAVORY'

(50) Latin Name: *Vaccinium ashei*
Varietal Denomination: Savory

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 10/613,314

(22) Filed: Jul. 7, 2003

(51) Int. Cl.[7] ..... A01H 5/00
(52) U.S. Cl. ..... Plt./157

(58) Field of Search ..... Plt./157

*Primary Examiner*—Kent Bell
*Assistant Examiner*—S B McCormick-Ewoldt

(57) ABSTRACT

A new and distinct low-chill rabbiteye blueberry (*Vaccinium ashei*) cultivar. Its novelty lies in the following unique combination of features:

1. Has a low chilling requirement.
2. Has a vigorous bush.
3. Produces large, medium-blue berries with small, dry picking scars and with good firmness, flavor and texture.
4. Ripens its crop early for a rabbiteye blueberry, averaging 7 to 10 days before 'Climax' (unpatented), or starting about May 22 in Homerville, Ga.

4 Drawing Sheets

Latin name of the genus and species: *Vaccinium ashei* Reade.

BLUEBERRY PLANT CALLED 'SAVORY'

Cross-reference to related applications. None.

Statement regarding federally sponsored research. None.

Variety denomination: Savory.

BACKGROUND OF THE INVENTION

Rabbiteye blueberries are native in the southeastern United States. During the past 30 years, improved cultivars have been developed, and these are now grown commercially for the fresh and processed markets on several thousand hectares of land in the southeastern United States, in Chile, Australia, and New Zealand. Rabbiteye blueberries tend to be more vigorous, more drought resistant, and tolerant of a wider range of soil types than highbush blueberries, but they have the disadvantage of late ripening. As a species, the wild rabbiteye blueberry tends to flower later than highbush blueberries growing in the same area, and the period from flowering to ripening is substantially longer for rabbiteye varieties. Thus, the harvest of highbush blueberries in eastern North Carolina normally begins before the harvest of rabbiteye blueberries much farther south in southern Georgia. This puts the rabbiteye blueberries at a market disadvantage compared to highbush. The late ripening also results in a less favorable harvest period with respect to weather. After early June, night temperatures and dew-point temperatures rise abruptly in north Florida and southeastern Georgia, and afternoon thunderstorms become much more frequent. The heat and rain interfere with harvest operations and lower berry quality.

Rabbiteye blueberry breeding began at the University of Florida about 1950, with the goal of developing early-ripening, disease-resistant plants that would produce high-quality berries in areas with mild winters. The principal method of breeding was recurrent selection, in which large numbers of seedlings were produced and evaluated after controlled crosses, and the best seedlings were used again as parents to produce the next cycle of seedlings. This process was carried out repeatedly as quickly as the seedlings could be evaluated for fruit quality and season of ripening. Because of the way the recurrent selection program was conducted, the two immediate parents of 'Savory' are not known. It is known that neither parental clone was patented. 'Savory' is a clonally-propagated selection from this program and is valuable because of its early ripening, large berry, and vigorous bush.

One hundred plants of 'Savory' were asexually propagated by softwood cuttings in Gainesville, Fla. in June 2001. The plants obtained were observed during two years of fruiting in the field, and they retained the distinctive characteristics of the clone. This test, along with previous propagations by softwood cuttings in Homerville, Ga., indicate that 'Savory' retains its distinctive characteristics and reproduces true to type in successive vegetative generations.

BRIEF SUMMARY OF THE INVENTION

'Savory' is a new rabbiteye blueberry variety that has the following unique combination of characteristics that set it apart from other blueberry cultivars.

a. Produces berries that average 2.0 g per berry on well-pruned plants compared to 1.4 g for the rabbiteye variety 'Climax' (unpatented).

b. Ripens its berries 7 to 10 days earlier than the variety 'Climax' (unpatented) when grown in southeast Georgia. Averages 25% of the crop ripe by May 22 at Homerville, Ga.

c. Has a chilling requirement of 300 hours per winter below 7° C.

d. Flowers at the same time as 'Climax' (unpatented), averaging full bloom in early March at Homerville, Ga.

e. Produces berries with a small, dry picking scar and high firmness.

f. Produces a vigorous, upright bush, reaching a height of 2 m within 4 years on favorable sites.

BRIEF DESCRIPTION OF THE DRAWING

The color chart used in this specification is "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are the more accurate.

DETAILED BOTANICAL DESCRIPTION

Figure 1:
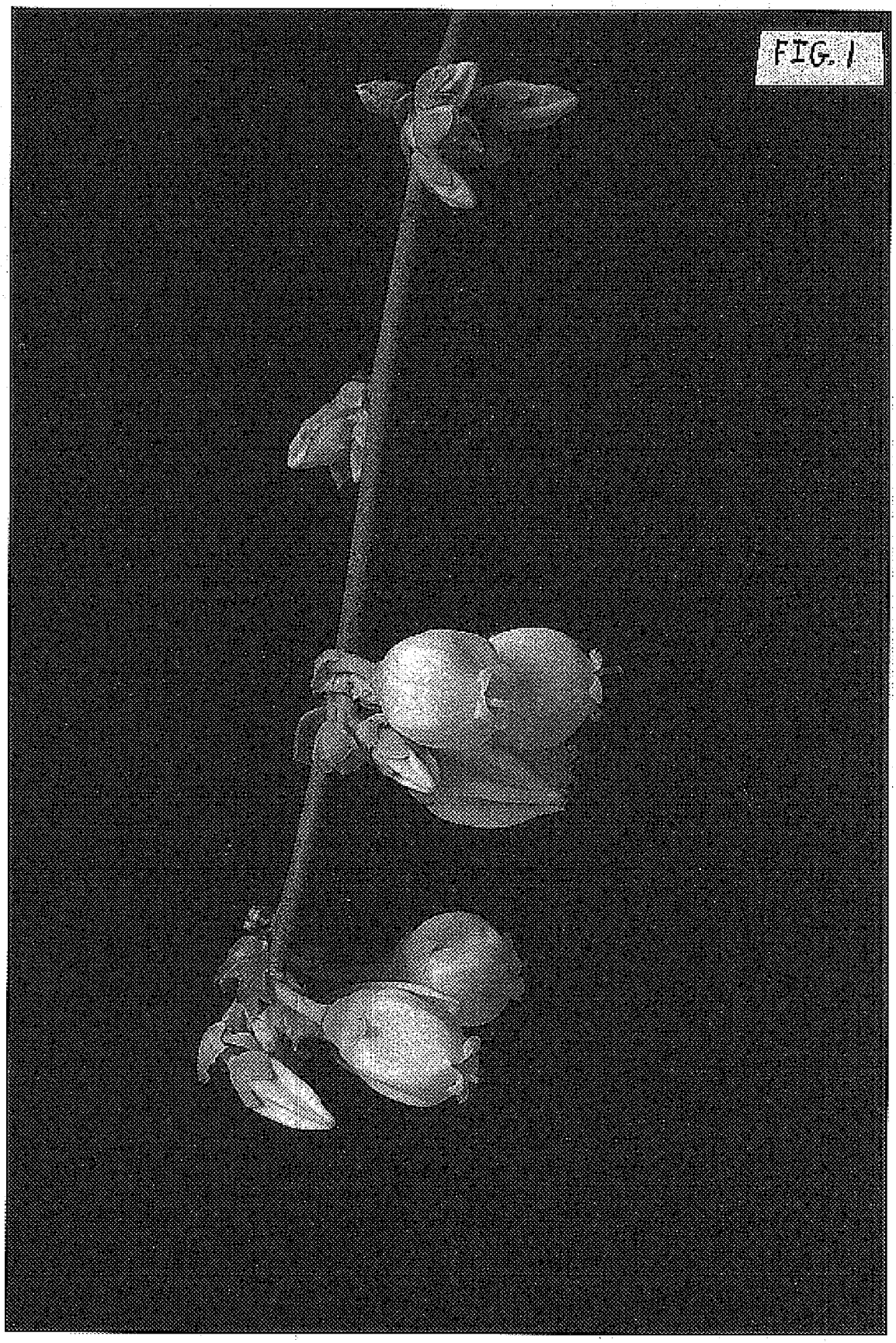
FIG. 1 shows several flower clusters of 'Savory', with some flowers fully open and others several days before opening. The tips of the styles are shown extending beyond the corolla tube of the open flowers.
Figure 2:
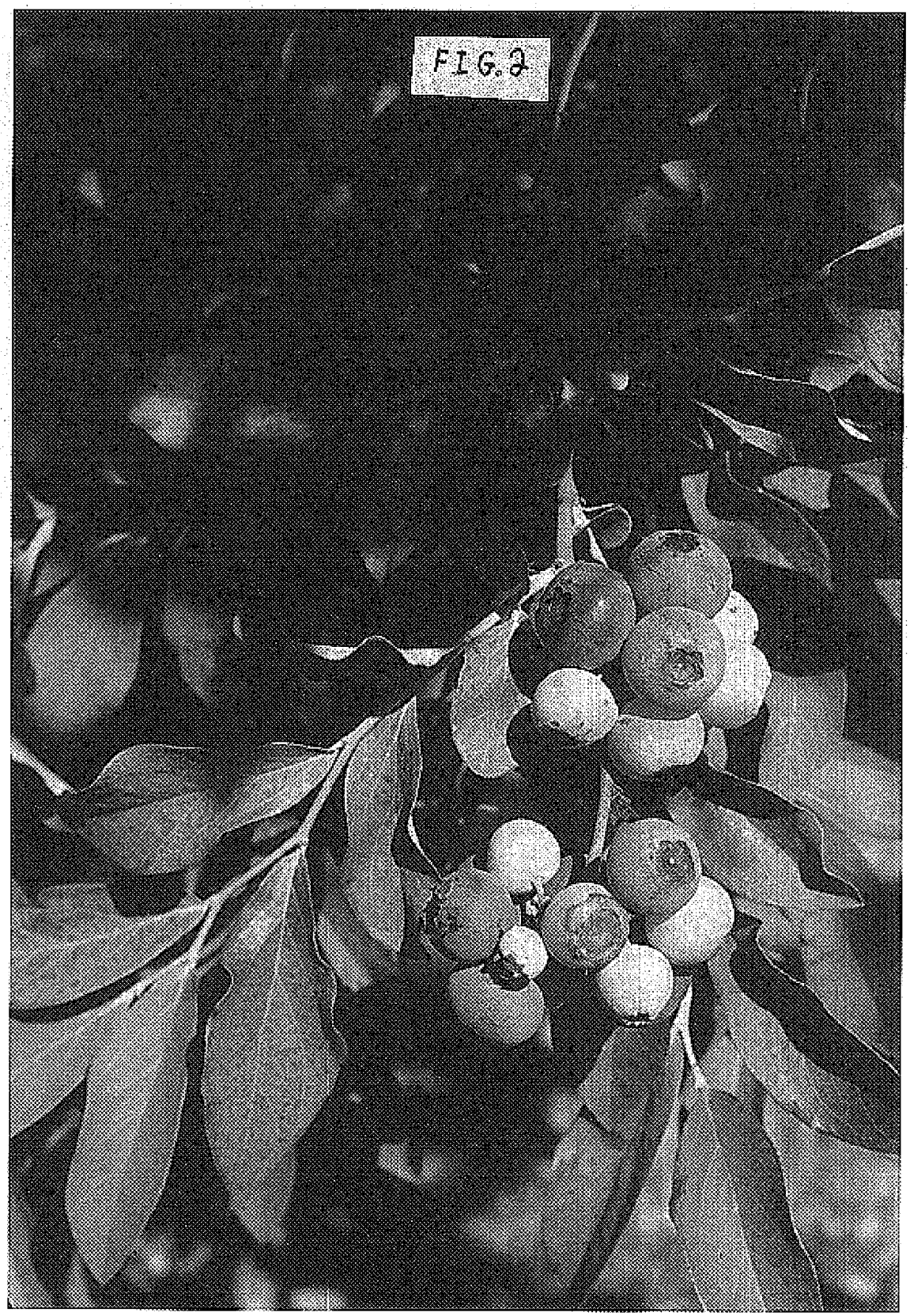
FIG. 2 shows clusters of berries 7 to 10 days before ripening, along with leaves of 'Savory'.
Figure 3:
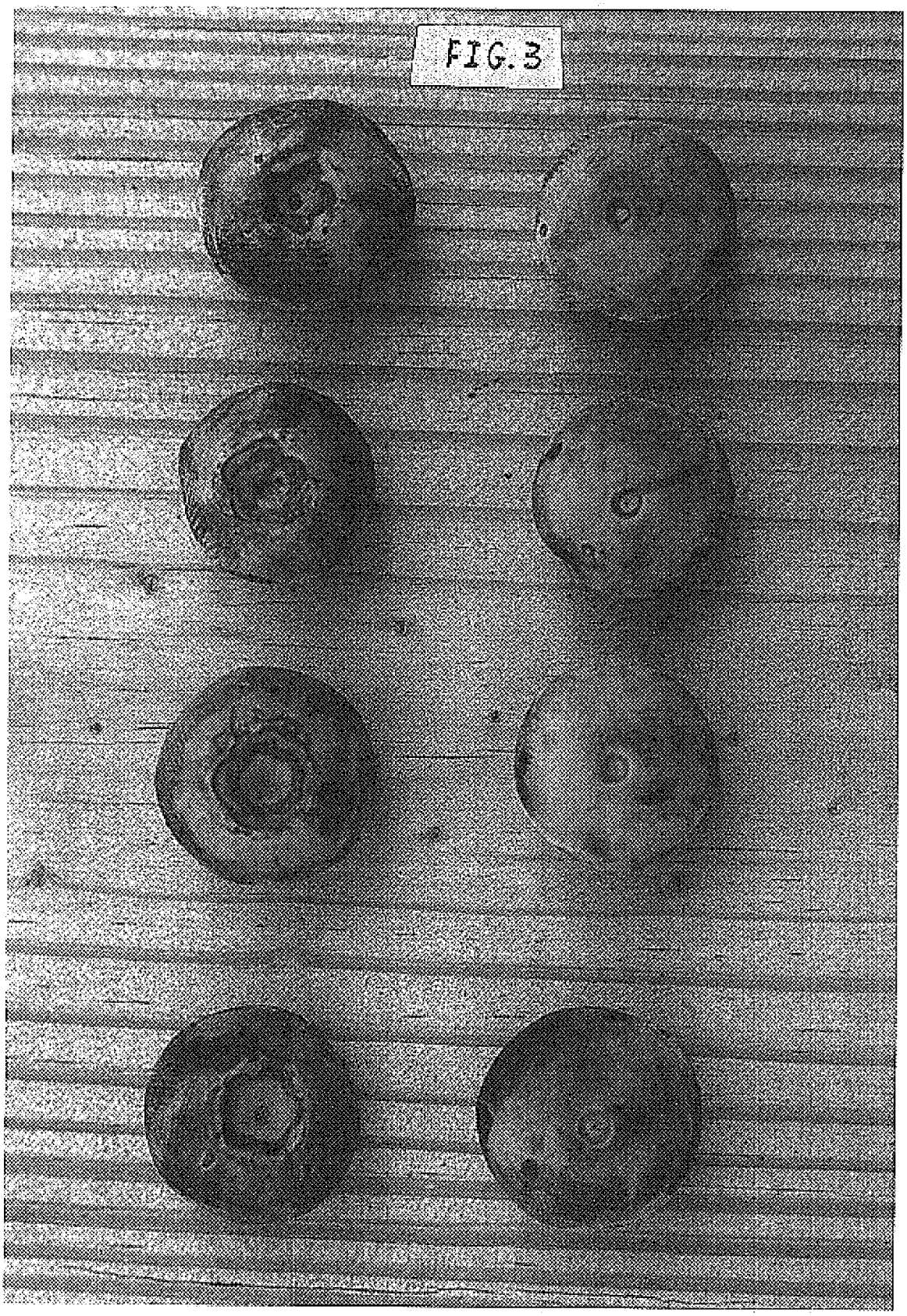
FIG. 3 shows ripe berries of 'Savory' in two orientations, one orientation showing the calyx end, with the broad, flat calyx aperture and poorly defined calyx lobes and the other orientation showing the small picking scar on the stem end of the berries.
Figure 4:
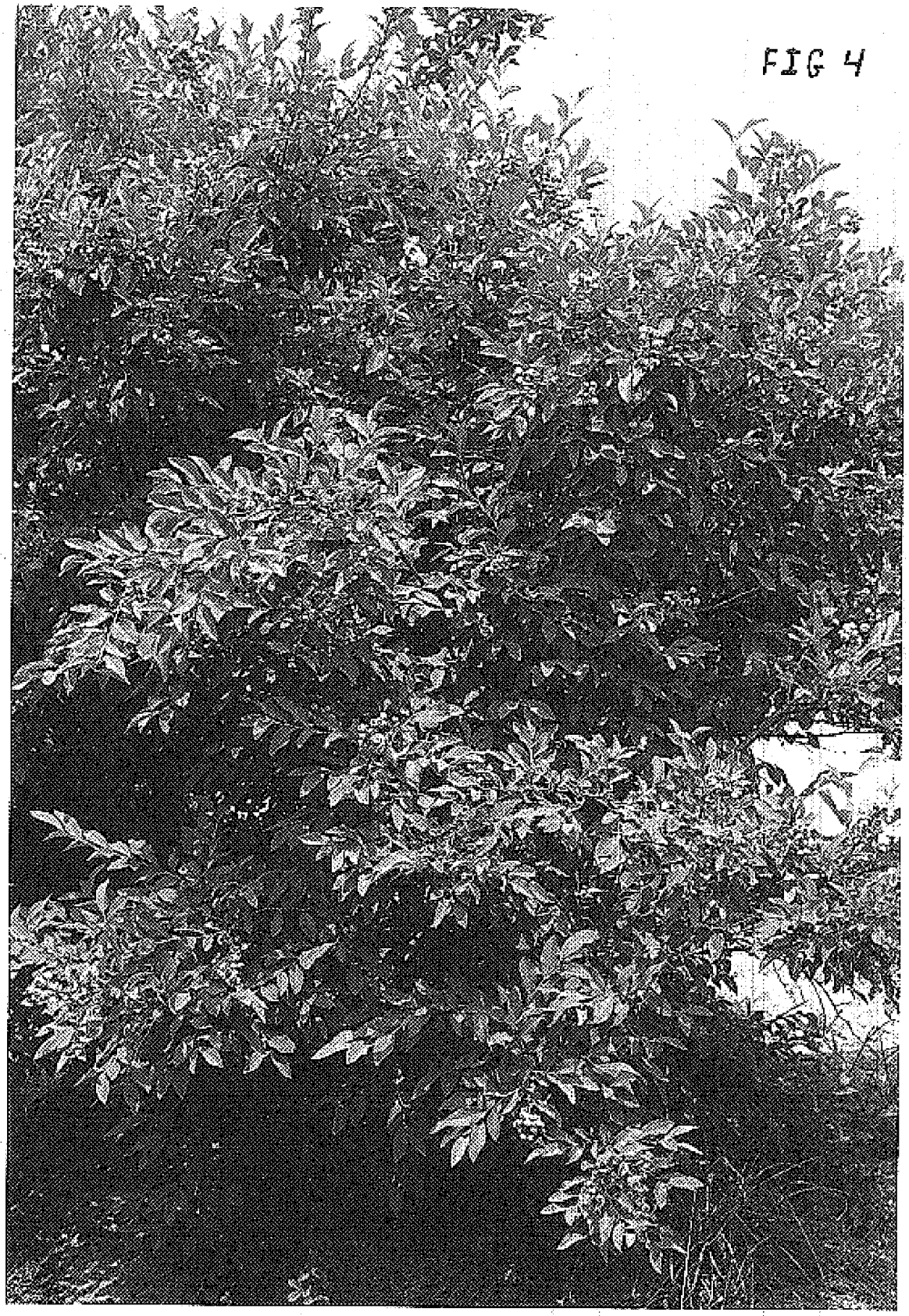
FIG. 4 shows a 10-year-old plant of 'Savory' bearing a light crop of berries (due to a hard, late freeze) in a field in Homerville, Ga. The plant is about 2.5 m tall.

Market class: 'Savory' produces rabbiteye blueberries suitable for both the fresh and processed fruit markets.

Bush: Unless otherwise indicated, plant characteristics were measured on 10-year-old plants in a commercial field in Homerville, Ga. The field had been irrigated, pruned, and managed in a way typical for commercial rabbiteye blueberry farms in southeast Georgia.

*Plant height.*—2.2 mm.

*Canopy diameter measured at widest part of the bush.*—2.3 m.

*Plant vigor.*—High. Equal to 'Brightwell' (unpatented).

*Growth habit.*—Individual shoots are upright, but numerous shoots from the base gives older plants a spreading form.

*Flower bud density (number) along flowering twigs in January.*—High.

*Twigginess.*—Low to medium.

*Diameter of largest canes, measured on 3-year-old plants 30 cm above the ground.*—18 mm.

Trunk and branches:

*Suckering tendency.*—High. Thirty major shoots were present from the base of 10-year-old plants.

*Surface texture of strong, 6-month old stems observed May 16.*—Smooth.

*Surface texture of strong, 1-year-old shoots observed May 16.*—Changing from smooth to rough as vertical cracks appear in the smooth stem and rough, corky bark fills the cracks.

*Surface texture of 3-year-old wood.*—Rough, but exfoliating to smooth.

*Diameter of strong branches from previous-summer's growth, measured in January, 30 cm from the tips on 3-year-old field-grown plants.*—3 mm.

*Color of 6-month-old wood on strong shoots viewed May 16.*—Sides of shoots most exposed to light: 'Hay', Pantone 12-0418; sides of shoots most shaded; 'Lily Green', Pantone 13-0317. Color of 1-year-old smooth wood viewed May 16. Sides of shoots most exposed to light: 'Burnt Sierra', Pantone 17-1544; sides of shoots most shaded: 'Hemp', Pantone 14-0721.

*Color of 3-year-old rough-textured canes viewed May 16.*—'Lark', Pantone 16-1324.

*Internode length on strong, upright shoots measured May 16.*—18 mm.

Leaves:

*Leaf length including petiole, from tip of petiole to end of blade.*—Mean=68 mm.

*Leaf width, widest point.*—29 mm.

*Leaf shape.*—Oval. Midrib terminates in a dew tip, which is about 0.4 mm long, visible under 15× microscope.

*Leaf margin.*—Minutely serrate.

*Color of upper surface of leaves.*—'Cameo Green', Pantone 14-6312.

*Color of lower surface of leaves.*—'Dewkist', Pantone 13-0107.

*Pubescence on upper surface of leaves.*—Some gland-tipped hairs on midrib visible at 15× magnification.

*Pubescence on lower surface of leaves.*—Numerous gland-tipped hairs conspicuous at 15×.

*Pubescence on leaf margins.*—Numerous gland-tipped hairs along margin visible at 15×.

*Relative time of leafing and flowering.*—Under normal spring conditions, the plants flower and begin to produce new leaves at nearly the same time.

Flowers:

*Flower arrangement.*—Flowers arranged alternately along a short, leafless, deciduous branch.

*Flower fragrance.*—None.

*Pedicel length at the time of anthesis.*—Mean 6 mm.

*Peduncle length at the time of anthesis.*—Mean 8 mm.

*Petals.*—Fused into a corolla tube with 5 lobes.

*Pollen staining.*—Approximately 99% of the pollen grains stain with acetocarmine dye, indicating that a high percentage of the pollen grains are well-formed, starch-filled, and potentially viable.

*Pollen abundance.*—Dried flowers shed pollen abundantly.

*Pollen color.*—'Straw', Pantone 13-0922.

*Flower type.*—Perfect, ovary inferior, petals fused into a corolla tube, the 10 stamens inserted at the base of the corolla tube.

*Flower length, pedicel attachment point to corolla tip.*—Mean 11 mm.

*Length of corolla tube.*—8 mm.

*Style length, top of ovary to stigma tip.*—10 mm.

*Calyx diameter at anthesis, tip of lobe to tip of opposite lobe.*—6 mm.

*Diameter of corolla tube at widest point.*—9 mm.

*Corolla aperture diameter.*—3 mm.

*Corolla surface texture.*—Smooth.

*Flower shape.*—Cylindro-urceolate.

*Corolla color at anthesis.*—White—the color of the unprinted spaces in the Pantone Book of Color.

*Calyx color at anthesis.*—'Piquant green', Pantone 17-0235.

*Pistil color at anthesis.*—Both style and ovary are 'Reed', Pantone 13-0215.

*Flowering period.*—Average time of 50% anthesis averages early March in Homerville, Ga. Flowering time is similar to 'Climax' (unpatented).

*Flower cluster.*—(tight, medium, or open). Medium.

*Average number of flowers per cluster.*—6.

*Location of the tip of the style relative to the lip of the corolla.*—The tip of the style extends beyond the lip of the corolla tube by 2 mm.

Berry:

*Mean date of first commercial harvest* (*25% fruit ripe*) *in Homerville, Ga.*—May 22 (7 to 10 days before 'Climax' (unpatented).

*Diameter of calyx aperture on mature berry.*—Mean 7 mm.

*Calyx lobes on mature berry.*—size and shape. Almost no calyx lobes.

*Berry cluster.*—(tight, medium, or open). Medium.

*Pedicel length of ripe berry.*—Mean 5.4 mm.

*Peduncle length of ripe berry.*—Mean 4.2 mm.

*Number of ripe berries per cluster.*—Mean 6.7.

*Mean berry weight on well-pruned plants.*—2.0 g compared to 1.4 g for 'Climax' (unpatented).

*Mean berry height.*—12.4 mm.

*Mean berry width.*—16.8 mm.

*Berry color* (*ripe*) *on plant.*—'Neutral Gray', Pantone 17-4402.

*Berry color* (*after harvest and packing*).—'Steel Gray', Pantone 18-4005.

*Berry skin color after polishing.*—'Shale', Pantone 19-3903.

*Internal flesh color of ripe berry.*—'Pearl', Pantone 12-1304.

*Berry surface wax.*—Medium in quantity and persistence.

*Berry pedicel scar.*—Small, dry.

*Berry firmness.*—High.

*Berry flavor.*—Sweet, subacid.

*Berry texture.*—Good; neither seeds nor grit problematic.

*Color of dried seeds.*—'Leather brown', Pantone 18-1142.

*Weight of well-developed, dried seeds.*—0.58 mg.

*Length of well-developed, dried seeds.*—2.4 mm.

*Width of well-developed, dried seeds.*—1.3 mm.

Physiological characteristics:

*Chilling requirement.*—300 hours per winter below 7° C.

*Cold hardiness.*—Flowers and fruit hardy to −3° C. The plant, during winter dormancy, is hardy to −15° C.

*Productivity.*—'Savory' averages about 10 pounds of berries per plant on plants 6 years old and older.

*Ease of propagation.*—'Savory' propagates readily from softwood cuttings.

Diseases, insects, mites:

*Phytophthora root rot.*—High. Appears to equal or surpass 'Climax' (unpatented) in resistance.

*Stem blight* (*Botryosphaeria dothidia*).—Medium to high resistance.

*Stem canker* (*Botryosphaeria corticis*).—Appears to have high resistance.

*Fungal leaf spots.*—About average for rabbiteye blueberry. Somewhat susceptible to powdery mildew (*Microsphaera penicillata* var. *vaccinii*). Fungicide sprays may be needed in summer to maintain leaf health in commercial plantings in humid climates.

*Overall survival in the field.*—Good. Survival appears to be equal to or greater than that of 'Climax' (unpatented).

I claim:

1. A new and distinct rabbiteye blueberry plant, substantially as illustrated and described, characterized by having a vigorous bush, a large, high-quality berry, and a ripening season that is unusually early for rabbiteye blueberry.

* * * * *